United States Patent [19]

Imuro et al.

[11] Patent Number: 4,946,877

[45] Date of Patent: Aug. 7, 1990

[54] PROCESS FOR PRODUCING BISPHENOL A

[75] Inventors: Shigeru Imuro; Yoshio Morimoto; Takashi Kitamura, all of Aichi, Japan

[73] Assignee: Mitsui Toatsu Chemicals, Inc., Tokyo, Japan

[21] Appl. No.: 307,639

[22] Filed: Feb. 7, 1989

[30] Foreign Application Priority Data

Feb. 10, 1988 [JP] Japan .................................. 63-27628

[51] Int. Cl.$^5$ ...................... C07C 37/20; C07C 39/16; C07C 37/68
[52] U.S. Cl. .................................... 568/727; 568/724; 568/728; 568/749
[58] Field of Search ................ 568/724, 727, 728, 749

[56] References Cited

U.S. PATENT DOCUMENTS 3,049,569  8/1962  Apel et al. .

FOREIGN PATENT DOCUMENTS

| 0112615 | 7/1984 | European Pat. Off. ............ 568/727 |
| 0227697 | 9/1985 | Fed. Rep. of Germany ...... 568/724 |
| 27-5367 | 12/1917 | Japan ................... 568/727 |
| 40-7186 | 4/1940 | Japan ................... 568/727 |
| 928329 | 6/1963 | United Kingdom ............... 568/724 |
| 991307 | 5/1965 | United Kingdom ............... 568/724 |
| 1052618 | 12/1966 | United Kingdom ............... 568/727 |

Primary Examiner—Werren B. Lone
Attorney, Agent, or Firm—Burns, Doane, Swecker & Mathis

[57] ABSTRACT

In a process for producing bisphenol A by reacting phenol and acetone in the presence of hydrochloric acid as a catalyst, the improvement comprising adding the water-containing phenol separated from the reaction product mixture in the purification stage to the reaction mixture containing phenol and acetone, in such an amount that the water content in the reaction mixture is within the range of 1 to 5 wt%, said water-containing phenol being obtained from the dehydrochlorination step of the reaction product mixture, condensing the distilled off gases and liquid-separating of the condensates.

7 Claims, No Drawings

PROCESS FOR PRODUCING BISPHENOL A

BACKGROUND OF THE INVENTION

The present invention relates to an improved process for producing high-purity 2,2-bis(4hydroxyphenyl)propane (referred to as bisphenol A hereinafter) in such a manner that the formation of by-products is suppressed.

Bisphenol A is a raw material for polycarbonate resins and epoxy resins. Bisphenol A used for polycarbonate resins is required to be colorless and highly pure.

Bisphenol A is produced by the condensation reaction of phenol with acetone in the presence of an acid catalyst and an optional co-catalyst such as a sulfur compound. The reaction product mixture contains, in addition to bisphenol A, the catalyst, unreacted acetone, unreacted phenol, water and by-products.

The by-products contain as major components 2-(2-hydroxyphenyl)-2-(4-hydroxyphenyl)propane (referred to as o,p'-isomer hereinafter) and Dianin's compound. Minor components include 2,4-di-[2-(4-hydroxyphenyl)isopropyl]-phenol (referred to as trisphenol hereinafter), polyphenols, and substances which cause discoloration of the end product. They have adverse effects on the performance of the resins produced from such a bisphenol A.

Examples of acidic catalysts for the condensation reaction include inorganic acids (such as hydrochloric acid) and strongly acidic ion-exchange resins.

The reaction which employs hydrochloric acid as a catalyst may be carried out at a low temperature so that the adduct of bisphenol A and phenol crystallizes out of the reaction product mixture as the reaction proceeds. The reaction in this manner is used for the production of high-purity bisphenol A because the o,p'-isomer, which is a major by-product, is isomerized into bisphenol A or p,p'-isomer during the reaction so that the formation of the by-product, o,p'-isomer can be reduced.

The formation of Dianin's compound, which is another major by-product, can be reduced to some extent by adding a mercapto compound to the reaction mixture, as disclosed in Japanese Patent Publication No. 5367/1952. However, this is not practical for industrial use because the mercapto compound needs a complicated procedure for separation thereof and gives an undesirable odor to the product. The formation of Dianin's compound can also be reduced by using excess phenol. However, this is uneconomical because the excess phenol has to be separated from bisphenol A eventually. Another disadvantage is an increased formation of the o,p'-isomer.

In the reaction that employs hydrochloric acid as a catalyst, it is possible to obtain high-purity bisphenol A if the catalyst concentration is increased, as disclosed in Japanese Patent Publication No. 7186/1965 and GB No. 1052618. According to the latter disclosure, hydrogen chloride should be fed to the reaction zone under a pressure of 3.5 kg/cm$^2$ or above. According to the former disclosure, the reaction starts with a mixture of reactants (acetone and phenol) and water (3 to 10 wt % of the reactants) and proceeds while the reaction zone is being supplied with hydrogen chloride gas in an amount sufficient to saturate the water in the reaction zone.

There is disclosed in Japanese Patent Laid-open No. 93347/1974 a method of increasing the reaction rate by adding water to the phenol-acetone liquid layer in an amount slightly more than the amount necessary to attain saturation. A disadvantage of this method is that the reaction needs excess hydrogen chloride and a large amount of energy is required for the removal of hydrogen chloride, water, and phenol from the reaction product mixture and the recovery of the desired product from the mixture of phenol, water, and hydrogen chloride. This leads to an increased production cost for the bisphenol A. Another disadvantage of adding water to the reaction mixture is that the solubility of bisphenol A in phenol increases in the presence of water, with the result that the isomerization reaction decreases and hence the ratio of o,p'-isomer to bisphenol A increases.

SUMMARY OF THE INVENTION

It is an object of the present invention to provide an improved process for producing high-purity bisphenol A by the reaction of phenol and acetone in the presence of hydrochloric acid, said process forming by-products and impurities in such a small amount that the purification process can be simplified.

It is another object of the present invention to provide a process for producing bisphenol A, said process requiring less energy for the recovery of unreacted phenol and hydrochloric acid catalyst from the reaction product mixture as compared with the conventional process.

In accordance with the present invention, there is provided a process for producing bisphenol A by the reaction of phenol and acetone in the presence of hydrochloric acid as a catalyst, wherein the improvement comprises adding the water-containing phenol separated from the reaction product mixture in the purification stage to the starting reaction mixture containing phenol and acetone, in such an amount that the water content in the reaction mixture is within the range of 1 to 5 wt %.

BRIEF EXPLANATION OF THE DRAWING

The accompanying drawing is a flow sheet showing one embodiment of the process of the present invention for producing bisphenol A.

DETAILED DESCRIPTION OF THE INVENTION

After the reaction, the reaction product mixture in slurry form is fed to a dehydrochlorination column in which the hydrogen chloride catalyst, water, and a small amount of phenol are removed. It is necessary for this stage to completely remove the water added to the reaction apparatus, the water formed by the reaction, and the saturated hydrochloric acid.

The bottom liquid of the dehydrochlorination column comprises a mixture containing bisphenol A. The bottom liquid is transferred to the purification stage in which the desired product is isolated in the usual way. On the other hand, gases distilled off of the dehydrochlorination column are subsequently condensed and thereafter, the condensate is separated into an upper layer composed mainly of phenol and a lower layer composed mainly of water by means of a liquid-separating apparatus.

According to a preferred embodiment of the present invention, the upper layer composed mainly of phenol obtained by condensing the distilled off gases from the dehydrochlorination step, followed by liquid-separating is used as "the water-containing phenol layer separated from the reaction product mixture in the purification stage" to be added to the starting reaction mixture containing phenol and acetone. According to another preferred embodiment of the present invention, the upper layer composed mainly of phenol and a part of the lower layer composed mainly of water as mentioned above are used in combination for the same purpose.

The above-mentioned upper phenol layer contains, preferably, 12 to 25 wt % of water and 5 to 10 wt % of hydrogen chloride, with the balance being phenol. On the other hand, the lower water layer contains, preferably, 5 to 15 wt % of phenol and 20 to 35 wt % of hydrogen chloride, with the balance being water.

According to the process of the present invention, the aforesaid water-containing phenol layer is added alone or in combination with a part of the lower water layer to the starting reaction mixture in such an amount that the water content in the reaction mixture is within the range of 1 to 5 wt %. If the water content exceeds 5 wt %, the ratio of o,p'-isomer to bisphenol A increases and the recovery of water and hydrogen chloride needs a large amount of energy as well as large-sized equipment. Even a trace amount of hydrogen chloride left unremoved in the column bottom decomposes and discolors bisphenol A in the subsequent purification stage.

The water-containing phenol layer separated from the reaction product mixture may be added to the starting reaction mixture before or after saturation with hydrogen chloride.

According to the process of the present invention, the amount of phenol is 4 to 12 times (in molar ratio) that of acetone and the reaction is carried out substantially in the absence of a solvent. A part of the starting phenol may be supplied from the phenol layer separated from the reaction product mixture as mentioned above.

The reaction is carried out under a pressure of atmospheric pressure to 2 kg/cm$^2$ at 30° to 85° C., preferably 35° to 60° C., under agitation. With the reaction temperature lower than 30° C., the reaction is slow; and with the reaction temperature higher than 85° C., the reaction yields a large amount of by-products. The reactor may be heated or cooled, if desired.

The reaction time varies depending on the reaction temperature; it ranges from 0.1 to 10 hours in the case of batchwise reaction carried out in a stirred reactor.

Before beginning the reaction, hydrogen chloride may be saturated in the starting reaction mixture. Alternatively, hydrogen chloride gas may be continuously fed into a reactor after starting the reaction so that the reactants are kept saturated with hydrogen chloride as the reaction proceeds while forming water.

Since the reaction is accompanied by the generation of heat, i.e. the heat of reaction, the heat of absorption of hydrogen chloride, and the heat of crystallization of the adduct of bisphenol A with phenol, it is preferred that hydrogen chloride is fed both before and during the reaction. The above-mentioned heat may be removed by external heat exchange so that the reaction temperature is controlled within the aforesaid range.

As the reaction proceeds, the adduct of phenol and bisphenol A crystallizes out from the reaction product mixture. As a result, the o,p'-isomer is isomerized into bisphenol A which is the p,p'-isomer in the liquid phase of the reaction product mixture, and the ratio of the o,p'-isomer to bisphenol A decreases in the reaction product mixture. The reaction forms only a small amount of Dianin's compound due to the effect of water.

The reaction product mixture thus-obtained is freed of water, catalyst, and excess phenol to give bisphenol A, which is subsequently formed into granules or flakes as the final product, with or without purification. A colorless, high-purity bisphenol A can be obtained in a conventional purification process, for example, simply by removing phenol after the adduct of bisphenol A and phenol has crystallized out.

The process of the invention will be described with reference to a flow sheet shown in the accompanying drawing.

Phenol 1 and acetone 2 as the starting materials are fed to a mixing tank 3. They are mixed with the upper layer 15 in the mixing tank 3. The resulting mixture is fed to a hydrochloric acid saturation column 6, into which hydrogen chloride gas 5 is blown until the column is saturated. The reactants enter a reactor 8 in which the reaction proceeds at a prescribed temperature for a prescribed period. During the reaction, hydrogen chloride gas 5' is blown into the reactor 8 so that it is kept saturated with hydrogen chloride. After completing the reaction, the reaction product mixture is transferred to a dehydrochlorination column 10, in which the hydrochloric acid catalyst, water, and a small amount of phenol are removed by distillation. The product 12 left after distillation is sent to the purification step. The gas 11 distilled off from the dehydrochlorination column 10 is condensed in a condenser 13 and the condensate is separated into the upper and lower layers by a liquid-separating apparatus 14. The upper layer 15 (phenol layer) is added to the starting reaction mixture according to the process of the present invention. The lower layer 16 (water layer) is partly added to the reaction mixture and the remainder is transferred to a stage for recovering hydrogen chloride and phenol.

Examples

The invention will be described in more detail with reference to the following working examples and comparative examples.

Example 1

The mixing tank was charged with 515 kg/hr of phenol and 58 kg/hr of acetone. To the phenol-acetone mixture was added 60 kg/hr of the upper layer (phenol layer) separated by the liquid-separating apparatus, said upper layer containing 12 wt % of water and 6 wt % of hydrogen chloride. The resulting phenol-acetone mixture containing 1.1 wt % of water and 0.6 wt % of hydrogen chloride was placed in a reactor having a capacity of 1.2 m$^3$ over one hour. The reaction was carried out under stirring while hydrogen chloride gas was being blown into the reactor so that it was kept saturated with hydrogen chloride. The reaction was completed after 8 hours. Upon analysis, the reaction product mixture in slurry form was found to contain 1.5 wt % of o,p'-isomer and 0.2 wt % of Dianin's compound based on the amount of bisphenol A and almost no trinuclear compound (or trisphenol).

Example 2

The same procedure as in Example 1 was repeated except that a part of the lower layer separated by the liquid-separating apparatus was further added, said lower layer containing 7 wt % of phenol and 32 wt % of hydrogen chloride. The mixing tank was charged with 512 kg/hr of phenol and 58 kg/hr of acetone. To the phenol-acetone mixture was added 60 kg/hr of the upper layer (phenol layer) and 35 kg/hr of the lower layer (water layer) separated by the separator. The resulting phenol-acetone mixture containing 4.3 wt % of water and 2.2 wt % of hydrogen chloride was placed in the reactor having a capacity of 1.2 m³ over one hour. The reaction was carried out under stirring while hydrogen chloride gas was being blown into the reactor so that it was kept saturated with hydrogen chloride. The reaction was completed after 8 hours. Upon analysis, the reaction product mixture in the form of a slurry was found to contain 1.6 wt % of o,p'-isomer and 0.2 wt % of Dianin's compound based on the amount of bisphenol A and almost no trinuclear compound.

Comparative Example 1

The same procedure as in Example 1 was repeated except that the upper layer separated by the separator was not added. The mixing tank was charged with 564 kg/hr of phenol and 58 kg/hr of acetone. Upon analysis, the reaction product mixture in slurry form was found to contain 1.7 wt % of o,p'-isomer and 0.8 wt % of Dianin's compound based on the amount of bisphenol A and 0.2 wt % of trinuclear compound.

Comparative Example 2

The same procedure as in Example 2 was repeated except that the lower layer separated by the separator was added excessively. The mixing tank was charged with 510 kg/hr of phenol and 58 kg/hr of acetone. To the phenol-acetone mixture was added 60 kg/hr of the upper layer (phenol layer) and 70 kg/hr of the lower layer (water layer) separated by the separator. The resulting phenol-acetone mixture containing 7.8 wt % of water and 4.1 wt % of hydrogen chloride was placed in the reactor having a capacity of 1.2 m³ over one hour. The reaction was carried out under stirring while hydrogen chloride gas was being blown into the reactor so that it was kept saturated with hydrogen chloride. The reaction was completed after 8 hours. Upon analysis, the reaction product mixture in slurry form was found to contain 2.0 wt % of o,p'-isomer and 0.2 wt % of Dianin's compound based on the amount of bisphenol A and almost no trinuclear compounds.

According to the process of the present invention, it is possible to reduce the formation of by-products and increase the reaction rate due to the effect of water. In addition, it is also possible to save energy for the recovery of phenol and hydrogen chloride due to the recycling of the upper layer (phenol layer) and a part of the lower layer (water layer) separated by the separator.

What is claimed is:

1. In a process for producing bisphenol A by reacting a reaction mixture comprised of phenol and acetone in the presence of hydrochloric acid as a catalyst at a temperature of 30° to 85° C. to produce a reaction product mixture which is subjected to dehydrochlorination, the improvement comprising adding water-containing phenol separated from the reaction product mixture during dehydrochlorination to the reaction mixture containing phenol and acetone, in such an amount that the water content in the reaction mixture is within the range of 1 to 5 wt %.

2. A process for producing bisphenol A as claimed in claim 1, wherein the water-containing phenol layer originates from an upper layer which is composed mainly of phenol, the upper layer being obtained by condensing gases distilled off from the reaction product mixture in the dehydrochlorination stage, followed by liquid-separating.

3. A process for producing bisphenol A as claimed in claim 1, wherein the water-containing phenol layer originates from an upper layer which is composed mainly of phenol and a part of a lower layer which is composed mainly of water, said two layers being obtained by condensing gases distilled off from the reaction product mixture in the dehydrochlorination stage, followed by liquid-separating.

4. A process for producing bisphenol A as claimed in claim 2, wherein the upper layer composed mainly of phenol contains further 12 to 25 wt % of water and 5 to 10 wt % of hydrogen chloride.

5. A process for producing bisphenol A as claimed in claim 3, wherein the upper layer composed mainly of phenol contains further 12 to 25 wt % of water and 5 to 10 wt % of hydrogen chloride, and the lower layer composed mainly of water contains further 5 to 15 wt % of phenol and 20 to 35 wt % of hydrogen chloride.

6. A process for producing bisphenol A as claimed in claim 1, wherein the reaction is carried out at a molar ratio of phenol to acetone of from 4:1 to 12:1.

7. A process for producing bisphenol A as claimed in claim 1, wherein the reaction is carried out by feeding hydrogen chloride gas continuously to maintain a saturation condition of hydrogen chloride in the reaction mixture throughout the reaction.

* * * * *

UNITED STATES PATENT AND TRADEMARK OFFICE
CERTIFICATE OF CORRECTION

PATENT NO.   :   4,946,877
DATED        :   August 7, 1990
INVENTOR(S)  :   Shigeru IIMURO ET AL.

It is certified that error appears in the above-identified patent and that said Letters Patent is hereby corrected as shown below:

Title page:

Item (75): inventor's name, amend "Imuro" to --Iimuro--.

Signed and Sealed this

Twenty-eighth Day of April, 1992

Attest:

HARRY F. MANBECK, JR.

*Attesting Officer*  *Commissioner of Patents and Trademarks*